(12) United States Patent
Rand et al.

(10) Patent No.: US 6,748,946 B1
(45) Date of Patent: *Jun. 15, 2004

(54) INHALATION DEVICE

(75) Inventors: Paul Kenneth Rand, Ware (GB); Gregor John McLennan Anderson, Ware (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/806,131

(22) PCT Filed: Sep. 23, 1999

(86) PCT No.: PCT/EP99/07078

§ 371 (c)(1),
(2), (4) Date: May 3, 2001

(87) PCT Pub. No.: WO00/18456

PCT Pub. Date: Apr. 6, 2000

(30) Foreign Application Priority Data

Sep. 26, 1998 (GB) .............................................. 9820937

(51) Int. Cl.[7] .............................................. A61M 16/00
(52) U.S. Cl. .............................. 128/203.15; 128/200.23
(58) Field of Search ....................... 128/200.12, 200.14, 128/200.17, 200.18, 200.21–200.23, 203.12, 203.14, 203.15, 203.21, 205.23, 200.24; 222/526, 533, 534, 182; 239/456

(56) References Cited

U.S. PATENT DOCUMENTS

| 3,151,618 A | | 10/1964 | Wakeman | |
|---|---|---|---|---|
| 3,191,867 A | | 6/1965 | Helms | |
| 3,622,053 A | * | 11/1971 | Ryden | 222/533 |
| 3,739,950 A | * | 6/1973 | Gorman | 222/533 |
| 4,114,811 A | | 9/1978 | Loeffler | |
| 4,130,116 A | | 12/1978 | Cavazza | |
| 4,509,515 A | * | 4/1985 | Altounyan et al. | 128/200.23 |
| 4,637,528 A | | 1/1987 | Wachinski et al. | |
| 4,641,644 A | * | 2/1987 | Andersson et al. | 128/200.23 |
| 4,796,614 A | * | 1/1989 | Nowacki et al. | 128/200.14 |
| 5,016,783 A | * | 5/1991 | Hayes et al. | 222/534 |
| 5,082,148 A | | 1/1992 | Dunning | |
| 5,085,347 A | * | 2/1992 | Hayes et al. | 222/534 |
| 5,284,133 A | | 2/1994 | Burns et al. | |
| 5,337,918 A | * | 8/1994 | Wang | 222/533 |

(List continued on next page.)

FOREIGN PATENT DOCUMENTS

| DE | 3639836 | 6/1998 |
|---|---|---|
| EP | 0028929 A | 5/1981 |

(List continued on next page.)

*Primary Examiner*—Aaron J. Lewis
*Assistant Examiner*—Teena Mitchell
(74) *Attorney, Agent, or Firm*—James P. Riek (57) ABSTRACT

There is provided an inhalation device suitable for dispensing medicament, particularly medicament for use in the treatment of respiratory disorders. The device comprises a body; a medicament carrier, locatable within said body; a mouthpiece, reversibly movable from a storage position wherein said mouthpiece is within the body to an in-use position wherein a portion of the mouthpiece protrudes from the body and wherein the mouthpiece is in communication with the medicament carrier to allow passage of medicament therebetween; and a mouthpiece actuator, movable relative to the body, and coupled to the mouthpiece such that movement of the mouthpiece actuator in a first direction moves the mouthpiece towards said storage position and movement of the mouthpiece actuator in an opposing direction moves the mouthpiece towards the in-use position. The device comprises no biassing means acting on the mouthpiece actuator.

21 Claims, 8 Drawing Sheets

U.S. PATENT DOCUMENTS

| | | |
|---|---|---|
| 5,347,998 A | 9/1994 | Hodson et al. |
| 5,347,999 A | 9/1994 | Poss et al. |
| 5,447,151 A | 9/1995 | Brunet et al. |
| 5,505,194 A | 4/1996 | Adjei et al. |
| 5,642,727 A * | 7/1997 | Datta et al. ............ 128/203.15 |
| 5,921,237 A | 7/1999 | Eisele et al. |
| 6,131,566 A * | 10/2000 | Ashurst et al. ........ 128/200.14 |
| 6,158,431 A | 12/2000 | Poole |
| 6,182,655 B1 | 2/2001 | Keller et al. |
| 6,223,746 B1 | 5/2001 | Jewett et al. |
| 6,260,549 B1 | 7/2001 | Sosiak |
| 6,273,084 B1 | 8/2001 | Frid |
| 6,401,712 B1 * | 6/2002 | von Schuckmann ... 128/203.15 |
| 6,422,236 B1 | 7/2002 | Nilsson et al. |
| 6,568,389 B1 * | 5/2003 | Rand et al. ............ 128/203.15 |
| 6,575,162 B1 * | 6/2003 | Rand ...................... 128/203.15 |

FOREIGN PATENT DOCUMENTS

| | | |
|---|---|---|
| GB | 2063075 | 6/1981 |
| GB | 2074454 | 11/1981 |
| WO | 9211051 | 7/1992 |
| WO | WO 93/09831 | 5/1993 |
| WO | WO 94/21317 | 9/1994 |
| WO | WO9940959 | 8/1999 |
| WO | WO 00/18456 | 4/2000 |
| WO | WO 00/18457 | 4/2000 |
| WO | WO 00/18458 | 4/2000 |

* cited by examiner

INHALATION DEVICE

CROSS REFERENCE TO RELATED APPLICATION

This application is filed pursuant to 35 U.S.C. §371 as a United States National Phase Application of International Application No. PCT/EP99/07078 filed Sep. 23, 1999, which claims priority from GB9820937.2 filed Sep. 26, 1998 in the United Kingdom.

BACKGROUND OF THE INVENTION

Field of the Invention

Description of the Related Art

The present invention relates to an inhalation device for use in the administration of medicament to a patient. The device has a mouthpiece, which is reversibly retractable from a storage position located inside the body of the device to a dispensing position in which the mouthpiece protrudes from the body of the device.

The use of inhalation devices in the administration of medicaments, for example in bronchodilation therapy, is well known. Such devices generally comprise a body or housing within which a medicament container is located. A mouthpiece (or nozzle) is typically provided, wherein 'in use' the mouthpiece communicates with the medicament container to allow passage of medicament from the source to the mouthpiece and thence, to the patient.

In a typical dispensing operation the body of the device is held by the patient and the mouthpiece (or nozzle) of the inhalation device is placed in the mouth (or nose) of the patient. The patient inhales, thereby causing transfer of medicament from the medicament container to the interior of the body of the patient.

When not in use it is desirable, from a hygiene standpoint, that the mouthpiece is provided with some kind of protective cover. The cover desirably acts both to prevent build-up of dirt on the mouthpiece and to prevent ingress of dirt into the body of the device through the mouthpiece, which might then be subject to inhalation by a patient.

It is known to provide the mouthpiece with a protective cap which acts as a protective cover. The cap may either be an entirely separate element or it may be joined to the body of the device in some way. DE-A-3,639,836, for example, describes a device in which the protective cap is mounted on an arm, which is pivotally mounted to the body of the device.

As an alternative to the use of a protective cap, one might envisage a device having a mouthpiece which is reversibly retractable from a storage position in which the mouthpiece is contained within the body of the device to a dispensing position in which the mouthpiece protrudes from the body of the device. In a device of this type the body of the device itself acts as the protective cover when the mouthpiece is in the storage position. The mouthpiece cover is thus an integral part of the inhalation device, avoiding contamination problems of prior art mouthpieces caused by loss of removable mouthpiece covers.

GB-A-2,074,454 describes an inhalation device comprising a tubular body adapted for detachable fitting to an aerosol container. A mouthpiece is provided, which is movable from a storage position to a dispensing position by means of a cap, rotatably mounted on the tubular body, which has biassed actuating means associated therewith. The cap and tubular body are provided with openings of similar dimensions. Manual rotation of the cap to bring the openings into register causes the biassed actuating means to urge the mouthpiece to the dispensing position in which the mouthpiece protrudes from the body of the device. Conversely, rotation of the cap by the user to bring the openings out of register causes the mouthpiece to be moved to the storage position in which the mouthpiece is contained within the body of the device.

The device described in GB-A-2,074,454 requires the use of biassed actuating means (e.g. resilient strip, elastic element), which urge the mouthpiece towards the dispensing position. A disadvantage associated with the use of such biassed actuating means is that they can be prone to mechanical failure (e.g. the overstretched spring or elastic band) or to becoming dislodged within the device (e.g. the 'lost spring'). Where the action of the device relies on the use of a biassed actuating means, such mechanical failure or dislodgement can lead to non-functioning of the device. In particular, the mouthpiece becomes irretrievable.

BRIEF SUMMARY OF THE INVENTION

The Applicants have now found that a device having a mouthpiece which is reversibly retractable from a storage position to a dispensing position can be constructed without reliance on any biassed actuating means.

According to one aspect of the present invention there is provided an inhalation device for dispensing medicament comprising a body;

a medicament carrier;

a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and a mouthpiece actuator, movable relative to the body, and coupled to the mouthpiece such that movement of said mouthpiece actuator in a first direction moves the mouthpiece towards said storage position and movement of the mouthpiece actuator in a second direction moves the mouthpiece towards said in-use position characterised in that the device comprises no biassing means acting on the mouthpiece actuator.

In particular, the device herein comprises no biassing means acting such as to bias the mouthpiece actuator towards either the in-use position or the storage position.

Herein the term 'mouthpiece' is used in a generic sense to mean an element shaped such as to be insertable into the mouth or nose of a patient for inhalation therethrough.

In one preferred aspect, the mouthpiece actuator and mouthpiece are coupled, for example, by a coupling mechanism. In one preferred aspect, the coupling mechanism comprises a rack and pinion mechanism. In another particularly preferred aspect, the coupling mechanism comprises a hinged lever mechanism.

In another preferred aspect, the mouthpiece actuator and mouthpiece are directly coupled. Preferably the mouthpiece actuator is a rotatable turning device directly coupled to the mouthpiece.

In one aspect, the medicament carrier is within the body. In another aspect, the medicament carrier is attachable to the exterior of the body.

Preferably, the mouthpiece is comprised of an elastic material.

Preferably, the mouthpiece is provided with a cover comprised of an elastic material.

Preferably, the inhalation device additionally comprises a curtain arrangement contactable by the mouthpiece on movement of the mouthpiece from the storage to the in-use position. More preferably, the curtain arrangement comprises a plurality of curtains comprised of an elastomeric material.

Preferably, the mouthpiece actuator is provided with a safety trigger mechanism to prevent accidental actuation thereof.

Preferably, at least a portion of the mouthpiece actuator is shaped for ease of grip by the user.

Preferably, at least a portion of the mouthpiece actuator has a friction-enhancing coating.

Preferably, the device is provided with a dose counter, which indicates the number of doses dispensed from or remaining in the container. More preferably, the dose counter comprises an indexing mechanism actuated by a predetermined movement of the medicament container relative to the body.

Preferably the mouthpiece is actuable by a sliding thumb motion.

Preferably, the medicament container is an aerosol or a dry-powder container.

According to another aspect of the present invention, there is provided the use of an inhalation device provided herein for dispensing medicament.

BRIEF DESCRIPTION OF THE SEVERAL VIEWS OF DRAWINGS

Preferred embodiments of the inhalation device according to the present invention will now be described with reference to the accompanying drawings in which.

DETAILED DESCRIPTION OF THE INVENTION

Figure 1:
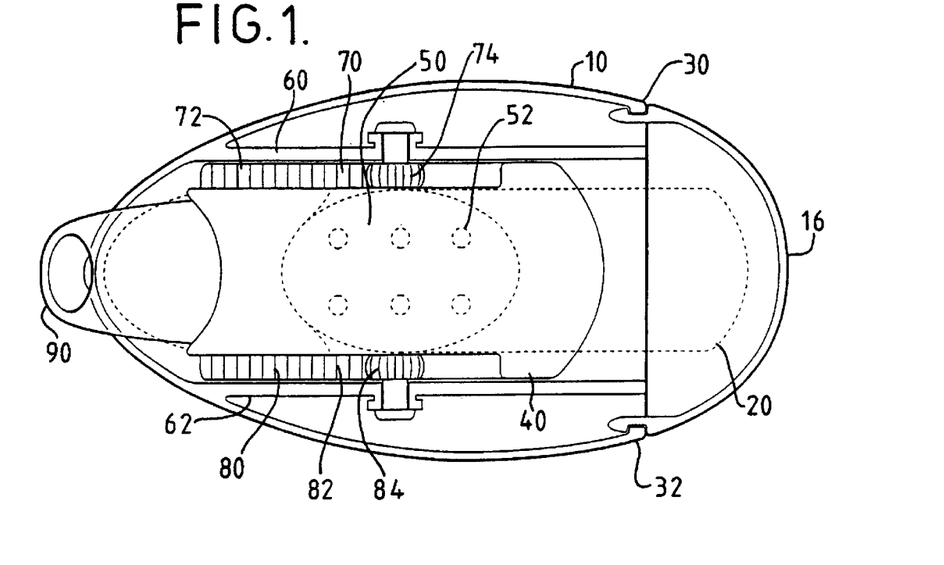
FIG. 1 is a sectional plan view of a first inhalation device in accord with the present invention.
Figure 2A:
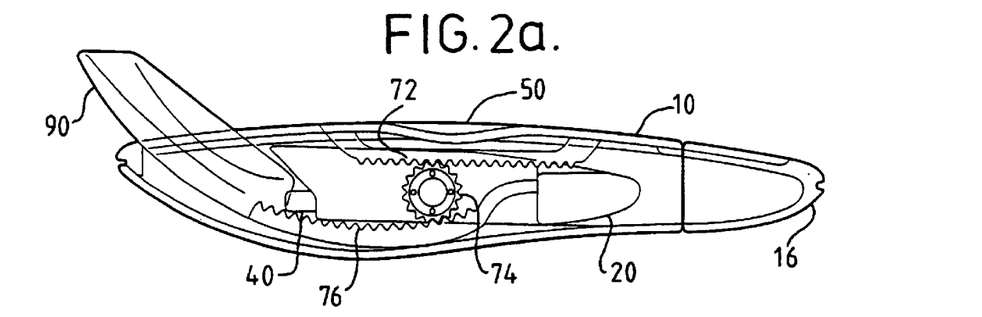
FIG. 2a is a sectional side view of the device of FIG. 1 and FIG. 2, wherein the mouthpiece is in the in-use position.
Figure 2B:
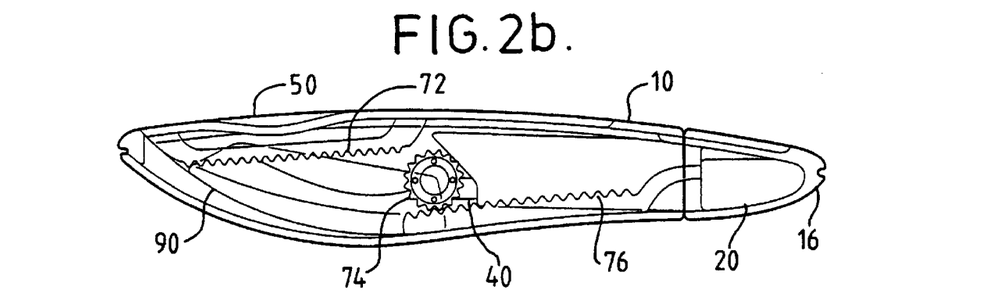
FIG. 2b is a sectional side view of the device of FIG. 1, wherein the mouthpiece is in the storage position.

FIGS. 1, 2a and 2b show a first inhalation device herein comprising a body 10 having an end cap 16, wherein the end cap 16 is reversibly attached to the body 10 by a snap fit mechanism 30, 32. Within the body there is provided a medicament container 20, which is in communication with a hollow transition piece 40 also provided in said body 10.

An essentially flat cover 50 is retainably mounted on first and second guide rails 60, 62 provided on a first face of the body 10 for slidable movement thereon. The exterior surface of the cover 50 has contours 52 for ease of grip by the user. The interior surface of the cover 50 communicates with first and second rack pinion mechanisms 70, 80 which are aligned with the axes defined by the first and second guide rails 60,62. Each of the first and second rack and pinion mechanisms 70, 80 (wherein, for clarity, only the first mechanism is shown in detail on FIGS. 2a and 2b) comprises a first rack 72, 82 attached to the cover 50, which communicates with a wheel 74, 84 axially mounted to the body 10, which wheel 74, 84 communicates with a curved second rack 76 which is mounted for communication with the mouthpiece 90.

Actuation of the device from the storage position (shown in FIG. 2a) to the in-use position) (shown in FIGS. 1 and 2b) is achievable by the user sliding the cover 50 along the guide rails 60, 62 in a direction towards the end cap 16. The first rack 72 is thus bought into engagement with wheel 74, which rotates and engages second rack 76, thereby moving the second rack 76 in the opposite direction. In turn, the movement of the second rack,76 causes the mouthpiece 90 to be moved to the in-use position, in which it protrudes from the body 10. In the in-use position it may be seen that the interior of the mouthpiece 90 communicates with the hollow interior of the transition piece 40, which itself communicates with the medicament container 20. Thus an inhalation passageway is provided from the mouthpiece 90 to the medicament container 20. Deactivation is achievable by the reverse sliding motion of the cover 50.

Figure 3A:
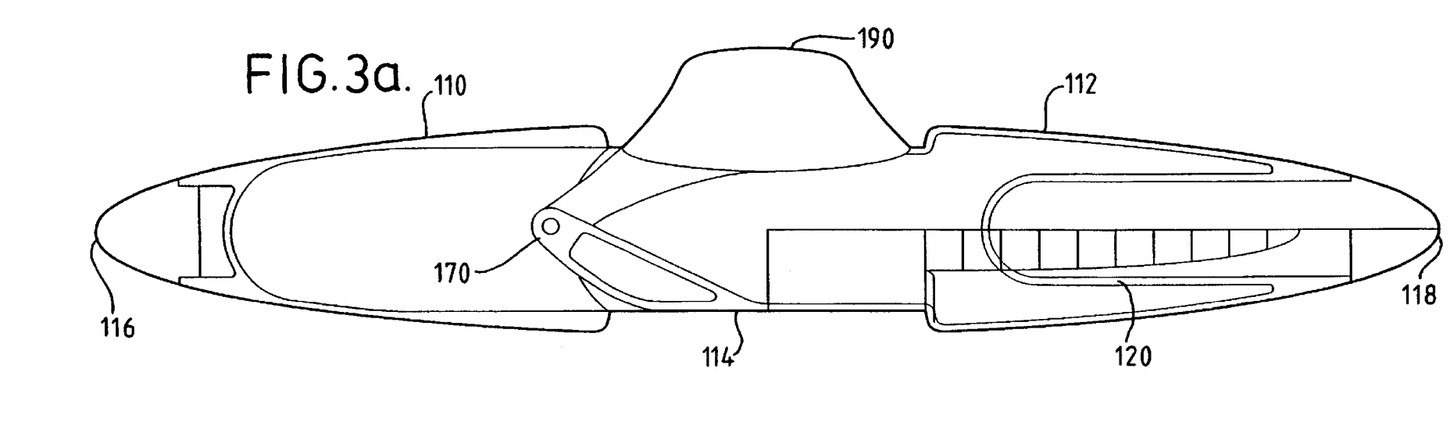
FIG. 3a is a sectional side view of a second inhalation device in accord with the present invention wherein the mouthpiece is in the storage position.
Figure 3B:
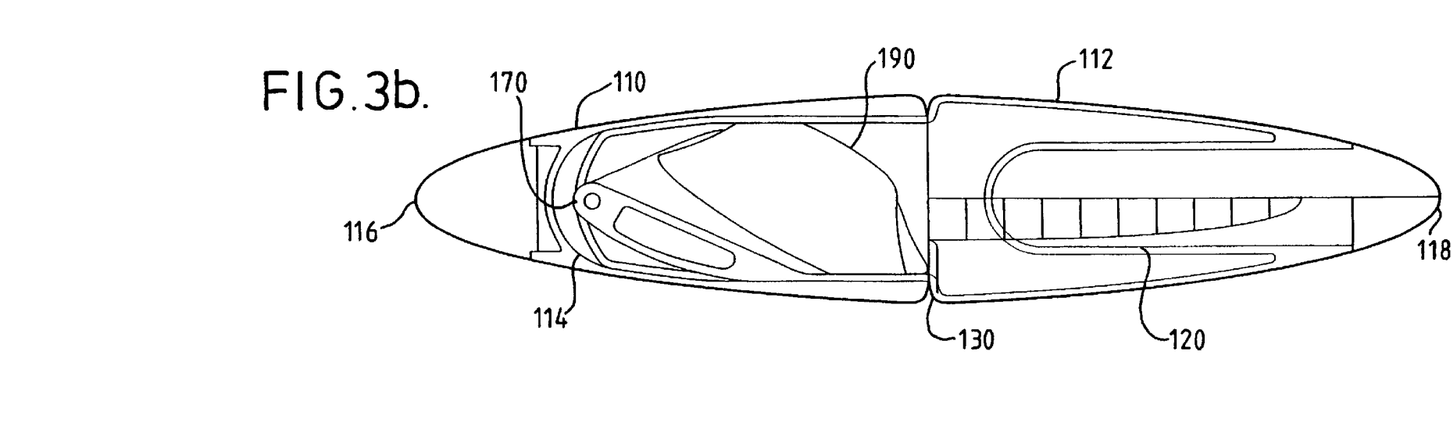
FIG. 3b is a sectional side view of the device of FIG. 3a wherein the mouthpiece is in the storage position.

FIGS. 3a and 3b show a second inhalation device herein having a flattened cigar shaped body comprising first 110 and second 112 body segments, wherein a male portion 114 of the second body segment 112 is slidably receivable within the interior of the first body segment 110, to form the full body-shape. When so received, the two body segments are releasably secured to each other by snap-lock mechanism 130. The first and second segments 110, 112 are provided with end caps 116, 118, which are coated with an elastomeric material for ease of grip thereof. A medicament cartridge 120 is provided within the second body segment 112. Mouthpiece 190 is coupled to the second body segment 112 through hinged arm mechanism 170.

Actuation of the device from the storage position (shown in FIG. 3b) to the in-use position (shown in FIG. 3a) is achievable by the user releasing the snap-lock 130 and slidably separating the first and second body segments 110, 112 away from each other. The movement of the second body segment 112 is translated to the mouthpiece 190 through the coupling provided by the hinged arm mechanism such that the mouthpiece 190 is moved to the in-use position. Deactivation is achievable by sliding the first and second body segments 110, 112 towards each other until the snap-lock 130 snaps into action.

Figure 4:
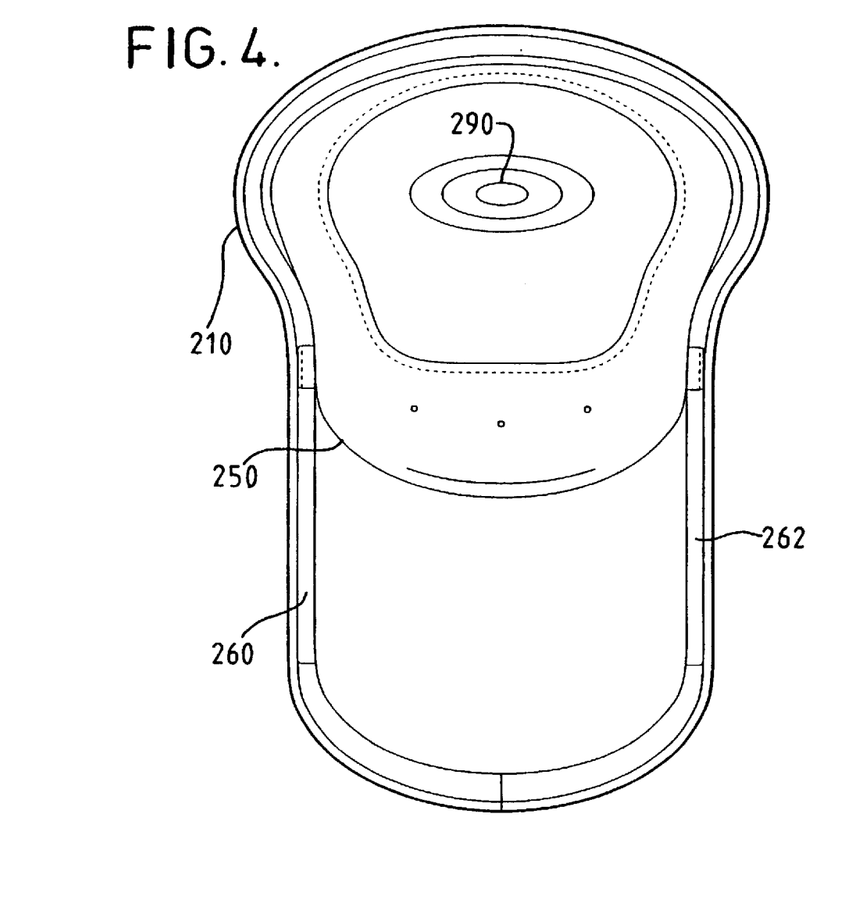
FIG. 4 is a sectional plan view of a third inhalation device in accord with the present invention.
Figure 5:
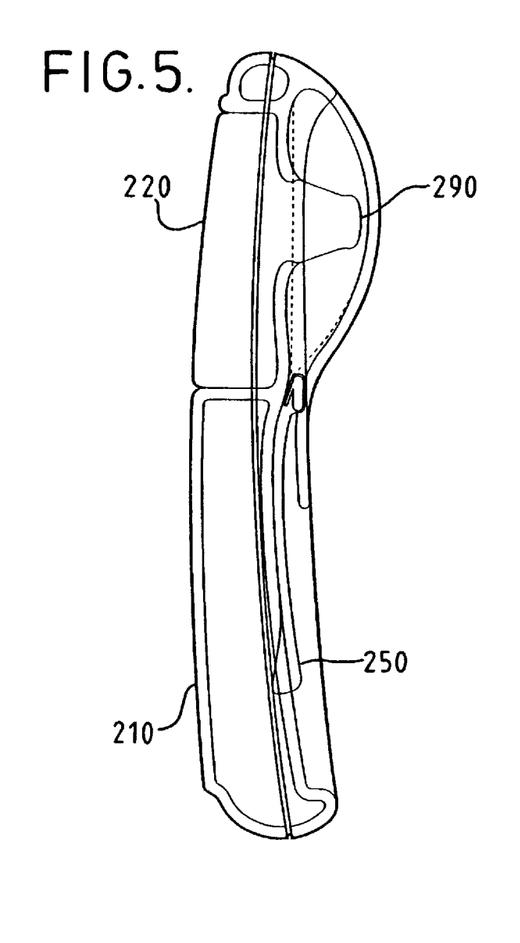
FIG. 5 is a sectional side view of the device of FIG. 5.

FIGS. 4 and 5 show a third inhalation device herein comprising a body 210, which is overall shaped for ease of grip in the hand of a user. Within the body 210 there is provided a medicament cartridge 220 and attached thereto mouthpiece 290, wherein the mouthpiece is comprised of a resiliently deformable elastomeric material. A shaped cover 250 is retainably mounted on first and second guide rails 260, 262 provided on the body 210 for slidable movement thereon.

Actuation of the device from the storage position (shown in FIG. 4) to the in-use position (shown in FIG. 5) is achievable by the user sliding the cover 250 along the guide rails 260, 262 (e.g. by a thumb movement), thereby revealing the mouthpiece 290, which 'pops out' into its characteristic shape. Deactivation is achievable by the reverse sliding action, which causes deformation of the mouthpiece 290.

Figure 6:
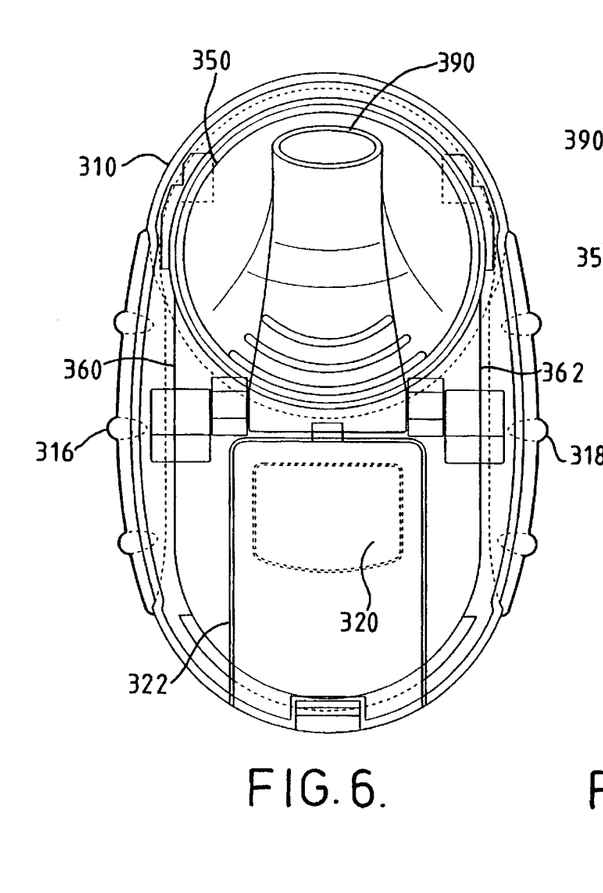
FIG. 6 is a sectional plan view of a fourth inhalation device in accord with the present invention.
Figures 7A, 7B:
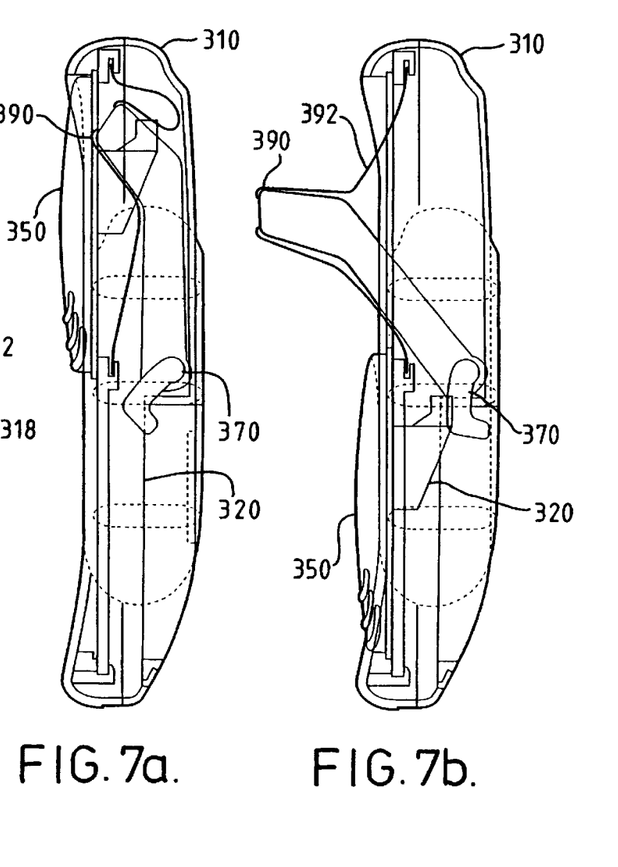
FIG. 7a is a sectional side view of the device of FIG. 6 wherein the mouthpiece is in the storage position.
FIG. 7b is a sectional side view of the device of FIG. 6 and FIG. 7a wherein the mouthpiece is in the in-use position.

FIGS. 6, 7a and 7b show a fourth inhalation device herein comprising a body 310 provided with a medicament compartment 320 which is accessible for loading of medicament by opening of door 322. Contoured elastomeric strips 316, 318 are provided to the body 310 for ease of grip thereof.

A circular, essentially flat cover 350 is retainably mounted on the first and second guide rails 360, 362 provided on the body 310. The interior surface of the cover 350 is coupled through articulated assembly 370 to mouthpiece 390, which is itself hingedly mounted. The mouthpiece 390 is provided with a thin, flexible elastomeric covering 392.

Actuation of the device from the storage position (shown in FIGS. 6 and 7a) to the in-use position (shown in FIG. 7b) is achievable by the user slidably moving the cover 350 along the guide rails 360, 362. The sliding action is coupled via articulated assembly 370 to the mouthpiece 390, which is moved to a position in which it stands proud from the body 310, and in which there is an inhalation passageway established between the mouthpiece 390 and the medicament compartment 320. Deactivation is achievable by performance of the reverse sliding action.

Figure 8A:
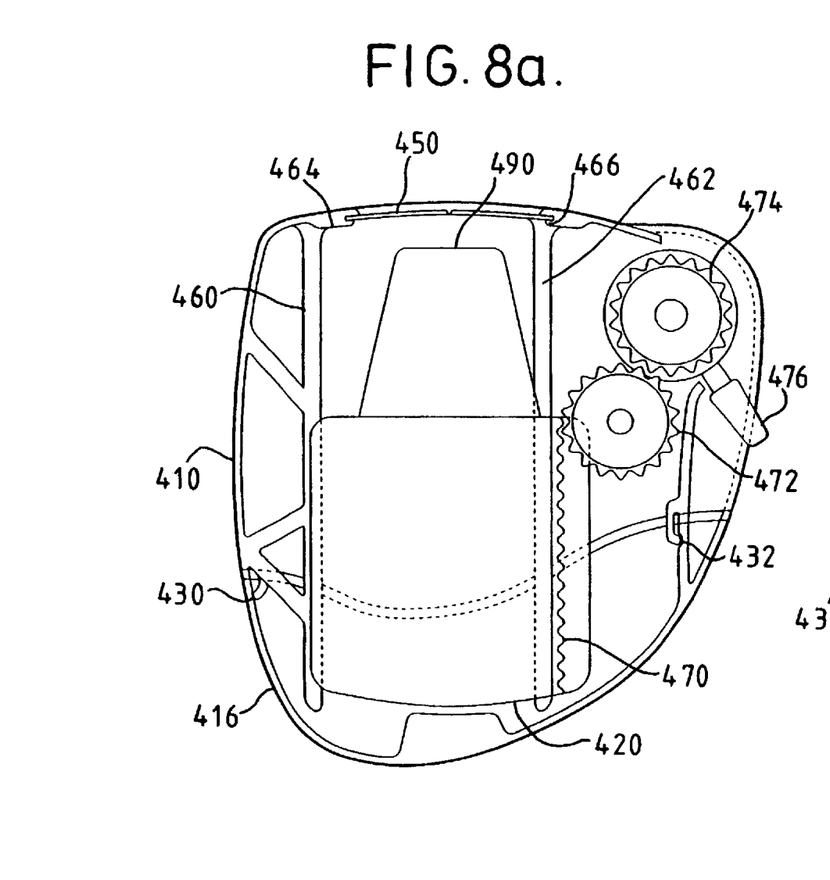
FIG. 8a is a sectional side view of a fifth inhalation device in accord with the present invention, wherein the mouthpiece is in the storage position.
Figure 8B:
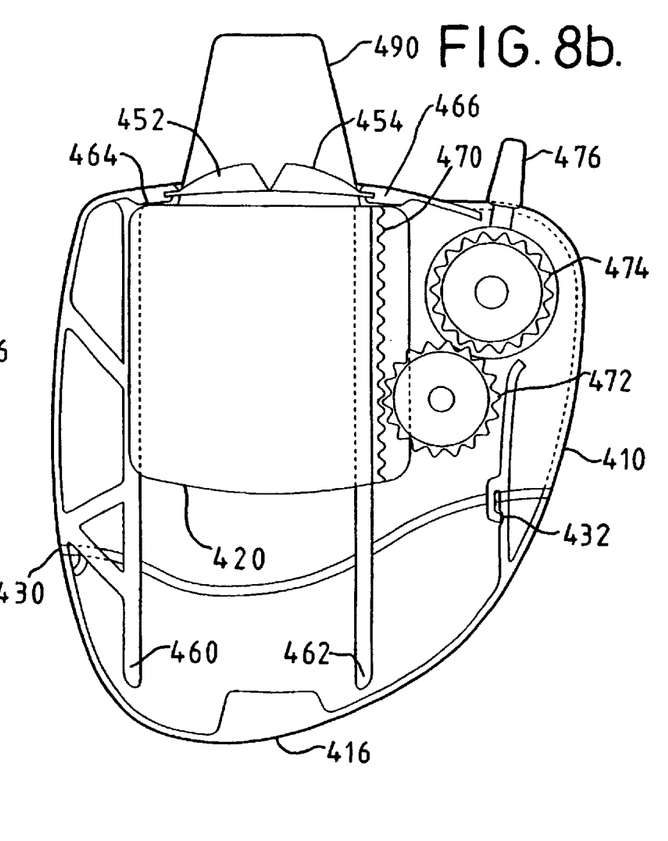
FIG. 8b is a sectional side view of the device of FIG. 8a, wherein the mouthpiece is in the in-use position.

FIGS. 8a and 8b show a fifth inhalation device herein comprising a body 410 having an end cap 416, wherein the end cap 416 is reversibly attached to the body 410 by a snap fit mechanism 430, 432. Within the body 410 there is provided a medicament container 420, and integral therewith a mouthpiece 490. In the storage position the mouthpiece 490 is kept protected from outside contamination by cover 450, which comprises an arrangement of elastomeric flaps 452, 454 forming a hygienic curtain. The integral medicament container 420 and mouthpiece 490 are mounted for translational movement on guide rails 460, 462. An outer face of the medicament container 420 is provided with a series of teeth forming a rack 470, which is in communication with first wheel 472 mounted for rotation on the body 410 thereby forming a rack and pinion mechanism. The first wheel 472 also communicates with second wheel 474, which is also mounted for rotation on the body 410. Rotation of the second wheel 474 is rotationally coupled to that of drive lever 476, which protrudes from the body 410 making it user accessible.

Actuation of the device from the storage position (shown in FIG. 8a) to the in-use position (shown in FIG. 8b) is achievable by a user-driven actuation of the drive lever 476. In practice, this can be achieved by a one-handed operation wherein the body 410 of the device is gripped between palm and fingers and the drive lever 476 is rotated by a motion of the thumb. It may be seen that rotation of the device lever 476 results in similar rotation of the second wheel 474 and opposite rotation of the first wheel 472, which engages with the rack 470 on the medicament container thereby driving the integral medicament container 420 and mouthpiece 490, upwardly along the guide rails 460, 462 to the in-use position. Ejection of the medicament container 420 from the body 410 is prevented by stops 464, 466.

It may also be seen that on actuation the mouthpiece 490 impacts with, and causes a parting, of the protective curtain arrangement 452, 454. In an improvement herein, the curtains 452, 454 may be provided with a friction cleaning surface or coating such that the mouthpiece is cleaned of any dust particles, dirt etc., when it contacts the curtains. Deactivation of the device is achievable by the reverse rotation of the drive lever 476.

Figures 9A, 9B:
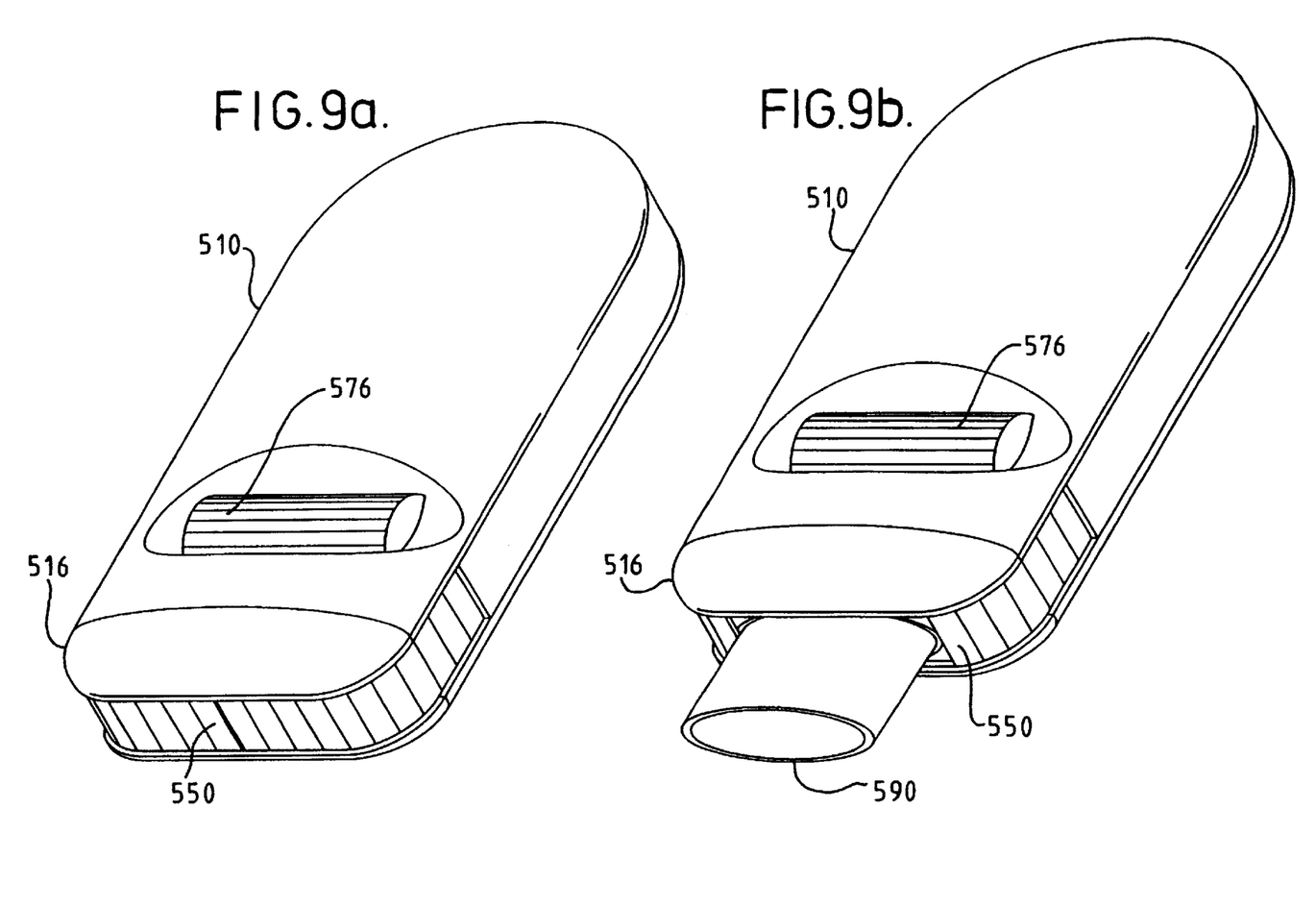
FIG. 9a is a perspective view of a sixth inhalation device herein, wherein the mouthpiece is in the storage position.
FIG. 9b is a perspective view of the device of FIG. 9a, wherein the mouthpiece is in the in-use position.

FIGS. 9a and 9b show a sixth inhalation device herein having an actuation mechanism (not shown in detail) similar to that of the device of FIGS. 8a and 8b. The device comprises a body 510 having a reversibly removable end cap 516. Within the body there is provided an integral medicament cartridge (not visible) and mouthpiece 590. A protective cover 550 is provided to the end cap 516, wherein the cover 550 prevents ingress of dirt and contamination to the mouthpiece 590 within the body 510. The drive lever 576 of the device of FIGS. 8a and 8b is replaced by a rotationally mounted drive cylinder 576, which has a grooved surface for ease of grip. It may be appreciated that the body 510 is shaped for ease of grip within the palm of a user's hand and the drive cylinder 576 is arranged for ease of rotation by a thumb motion. Actuation of the device is achievable by rotation of the drive cylinder 576 towards the end cap 516 and deactivation is achievable by the reverse rotatory movement.

Figure 10A:
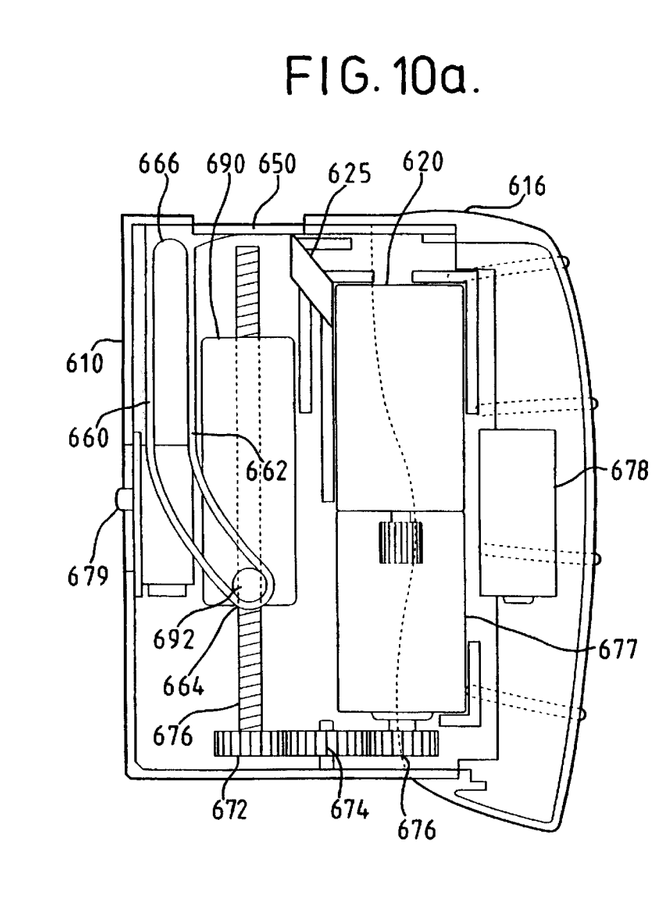
FIG. 10a is a sectional side view of a seventh inhalation device herein, wherein the mouthpiece is in the storage position.
Figure 10B:
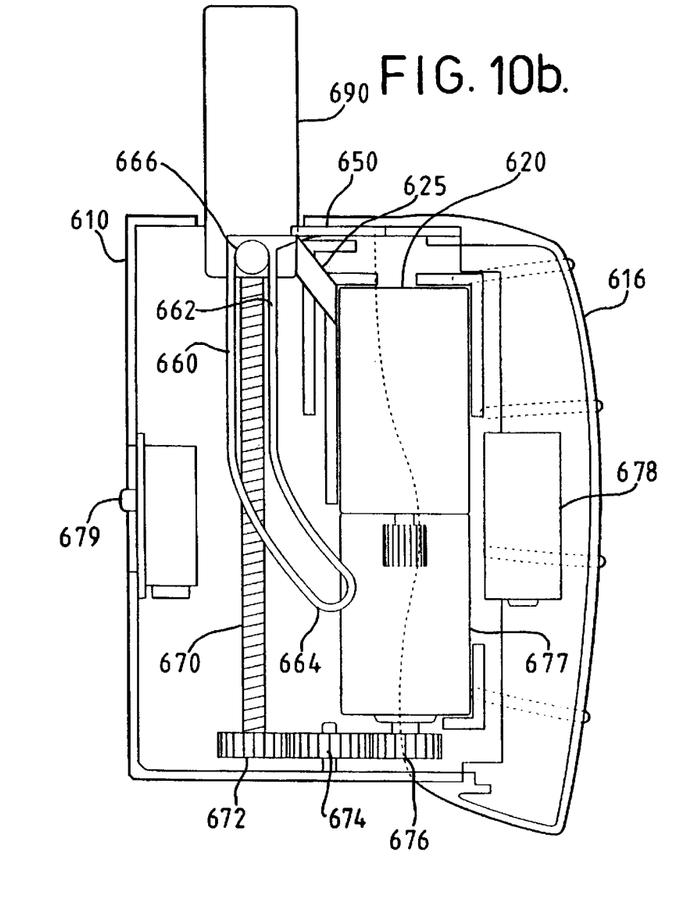
FIG. 10b is a sectional side view of the device of FIG. 10a, wherein the mouthpiece is in the in-use position.

FIGS. 10a and 10b show a seventh inhalation device herein comprising a body 610 having a reversibly detachable side position 616, which is shaped for ease of grip. Within the body 610 there is provided a medicament container 620. Also provided is mouthpiece 690, which communicates with the medicament container 620 through connecting passage 625 when the mouthpiece 690 is in the in-use position. The mouthpiece 690 is mounted on worm 670, such that the worm 670 is rotationally movable therewithin. The worm 670 is provided at the lower end with a worm drive wheel 672, which communicates with a second wheel 674 mounted on the body 610, which second wheel 674 communicates with a motor drive wheel 676. The motor drive wheel is driven by motor 677 powered by battery 678. A user accessible switch 679 is provided for actuation of the motor 678.

Rotation of the mouthpiece 690 is prevented by the presence of stub 692 on the mouthpiece 690. The stub 692, and hence mouthpiece 690, is mounted on movable guide rails 660, 662 having first and second end stops 664, 666 corresponding respectively to the mouthpiece storage and in-use positions. The upper end 666 of the movable guide rail arrangement 660, 662 is attached to a sliding door 650. The sliding door 650 is closed when the mouthpiece 690 is in the storage position thereby forming a protective cover. The door 650 is slidably openable in response to actuation of the mouthpiece 690, thereby allowing the mouthpiece 690 to protrude through the door opening.

Actuation of the device from the storage position (shown in FIG. 10a) to the in-use position (shown in FIG. 10b) is achievable by user actuation of the switch 679. It may be appreciated that the device as a whole is shaped for one-handed operation involving gripping of the end cap 616 by the fingers and thumb actuation of the switch 679. On actuation the motor 677 rotationally drives motor drive wheel 676, in turn causing rotation of the second wheel 674, worm drive wheel 672 and hence worm 670. The upward rotational movement of the worm 670 causes the mouthpiece 690 and stub 692 thereon to be driven upwards along a path defined by the axis of rotation of the worm 670.

Since the stub 692 is mounted on the guide rail arrangement 660, 662, it may be seen that the upwards movement of the stub 692 causes the shaped guide rails 660, 662 to be driven sideways (from left to right as shown), hence enabling opening of the sliding door 650, which is itself attached to the upper end 666 of the guide rail arrangement 660, 662.

Deactuation of the device is achievable by a second actuation of the switch 679, which results in the opposite motor-driven rotation of the gear assembly 672, 674, 676 and worm drive 670.

Figure 11A:
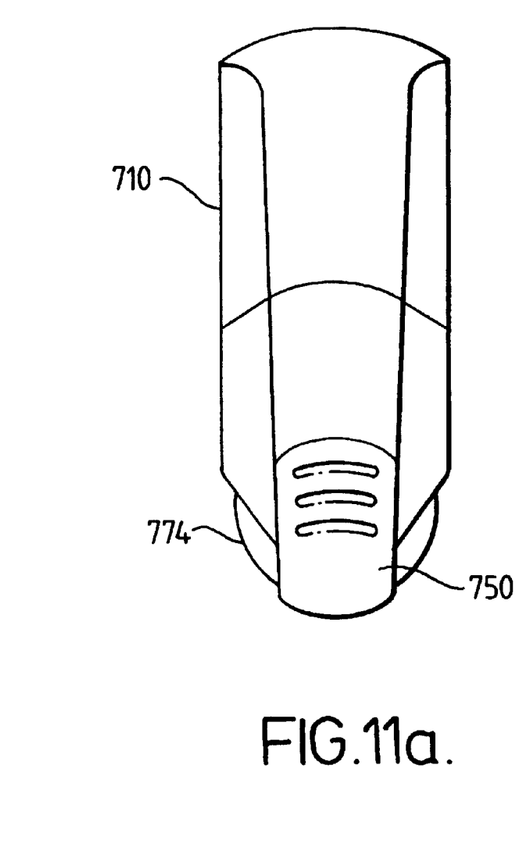
FIG. 11a is a front view of an eighth inhalation device herein, wherein the mouthpiece is in the storage position.
Figure 11B:
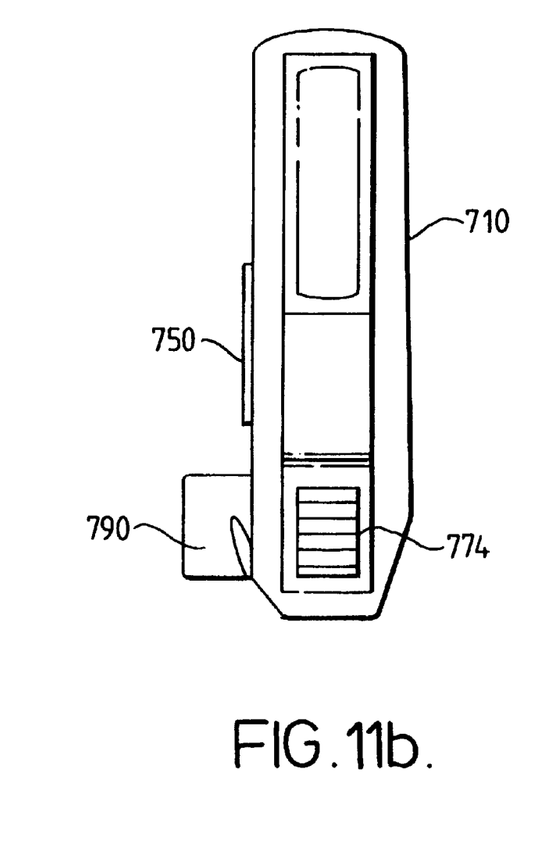
FIG. 11b is side view of the device in FIG. 11a, wherein the mouthpiece is in the in-use position.

FIGS. 11a and 11b show an inhalation device herein comprising a body 710, within said body 710 there is provided a hidden mouthpiece 790 and a medicament cartridge (not visible). A protective cover 750 of the mouthpiece 790 is provided which prevents ingress of dirt and contamination to the mouthpiece 790 within the body 710. The protective cover 750 is reversibly slidable to expose or cover hidden retracted mouthpiece 790.

There is provided a rotationally mounted drive cylinder 774, which has a grooved surface for ease of grip. It may be appreciated that the body 710 is shaped for ease of grip within the palm of a user's hand and the drive cylinder 774 is arranged for ease of rotation by a thumb motion. Actuation of the mouthpiece 790 is achievable by rotation of the drive cylinder 774 and deactuation is achievable by the reverse rotary movement.

The inhalation device herein is suitable for dispensing medicament, particularly for the treatment of respiratory disorders. Appropriate medicaments may thus be selected from, for example, analgesics, e.g. codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl) ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. An inhalation device for dispensing medicament comprising
   a body;
   a medicament container;
   a mouthpiece, reversibly movable from a storage position wherein said mouthpiece is within said body to an in-use position wherein a portion of the mouthpiece protrudes from the body and wherein the mouthpiece is in communication with said medicament container to allow passage of medicament therebetween; and
   a mouthpiece actuator, movable relative to the body by the linear movement of the thumb of a user, and coupled to the mouthpiece such that movement of said mouthpiece actuator in a first direction moves the mouthpiece towards said storage position and movement of the mouthpiece actuator in a second direction moves the mouthpiece towards said in-use position mouthpiece actuator is discrete from the mouthpiece and in an unbiased relationship therewith —substituted therefor 2. An inhalation device according to claim 1, wherein the mouthpiece actuator and mouthpiece are coupled by a coupling mechanism.

3. An inhalation device according to claim 2, wherein the coupling mechanism comprises a rack and pinion mechanism.

4. An inhalation device according to claim 2, wherein the coupling mechanism comprises a hinged lever mechanism.

5. An inhalation device according to claim 1, wherein the mouthpiece actuator and mouthpiece are directly coupled.

6. An inhalation device according to claim 5 wherein the mouthpiece actuator is a rotatable turning device coupled to the mouthpiece.

7. An inhalation device according to claim 1, wherein the medicament carrier is within the body.

8. An inhalation device according to claim 1, wherein the medicament carrier is attachable to the exterior of the body.

9. An inhalation device according to claim 1, wherein the mouthpiece is comprised of an elastic material.

10. An inhalation device according to claim 1, wherein the mouthpiece is provided with a cover comprised of an elastic material.

11. An inhalation device according to claim 1, additionally comprising a curtain arrangement contactable by the mouthpiece on movement of the mouthpiece from the storage to the in-use position.

12. An inhalation device according to claim 11, wherein said curtain arrangement comprises a plurality of curtains comprised of an elastomeric material.

13. An inhalation device according to claim 1, wherein the mouthpiece actuator is provided with a safety trigger mechanism to prevent accidental actuation thereof.

14. An inhalation device according to claim 1, wherein at least a portion of the mouthpiece actuator is shaped for ease of grip by the user.

15. An inhalation device according to claim 1, wherein at least a portion of the mouthpiece actuator has a friction-enhancing coating.

16. An inhalation device according to claim 1, wherein the medicament container is an aerosol container.

17. An inhalation device according to claim 1, wherein the medicament container is a dry-powder container.

18. An inhalation device according to claim 1, wherein the device is provided with a dose counter.

19. An inhalation device according to claim 18, wherein the dose counter comprises an indexing mechanism actuated by a predetermined movement of the medicament container relative to the body.

20. An inhalation device according to claim 1, actuable by a sliding thumb motion.

21. Use of an inhalation device according to claim 1 for dispensing medicament.

* * * * *